US00PP10085P

United States Patent [19]

Gerawan

[11] Patent Number: Plant 10,085

[45] Date of Patent: Oct. 28, 1997

[54] 'PRIMA GATTIE' PEACH TREE

[76] Inventor: Michael R. Gerawan, 6407 Englehart, Reedley, Calif. 93654

[21] Appl. No.: 593,528

[22] Filed: Jan. 24, 1996

[51] Int. Cl.[6] ..... A01H 5/00

[52] U.S. Cl. ..... Plt./43.1

[58] Field of Search ..... Plt./43.1

[56] References Cited

U.S. PATENT DOCUMENTS

P.P. 2,144 5/1962 Merrill ..... Plt./43.1

*Primary Examiner*—James R. Feyrer

*Attorney, Agent, or Firm*—Worrel & Worrel

[57] ABSTRACT

A new and distinct variety of peach *Prunus persica*, tree substantially as illustrated and described which produces large fruit which are mature for commercial harvesting and shipment approximately September 2 to September 19 in the San Joaquin Valley of central California and somewhat remotely similar to the fruit of the "Carnival" peach tree, but distinguished therefrom in numerous respects including that they are a semi-clingstone fruit with an improved blush coloration and a sweeter, more pleasant flavor when compared with the fruit of the "Carnival" peach tree.

1 Drawing Sheet

BACKGROUND OF THE NEW VARIETY

The present invention relates to a new and distinct variety of peach tree, which will hereinafter be denominated varietally as "Prima Gattie" peach tree, and, more particularly, to a peach tree which produces semi-clingstone fruit, which are mature for commercial harvesting and shipment approximately September 2 to September 19 in the San Joaquin Valley of central California.

Commercially acceptable fruit is abundant in the case of many varieties of fruit trees. This is particularly true of peach trees. The plentiful quantities of such commercially acceptable fruit result in there being a substantial market for such fruit throughout most of a comparatively long growing season.

However, commercially acceptable fruit is relatively rare at the initiation and termination of the growing season. Most such early or late ripening peach varieties produce fruit which is only marginally acceptable on a commercial basis in that it is small in size, or possesses poor skin coloration, or lacks desirable flavor, or has poor handling characteristics, or any combination of these and other negative characteristics. Accordingly, new peach varieties producing fruit which ripens early or late in the season, but which possesses characteristics more typical of fruit ripening more nearly at the height of the growing season are of significant commercial value. The new variety of peach tree of the present invention appears to be such a variety, as will hereinafter be set forth in greater detail.

ORIGIN AND ASEXUAL REPRODUCTION OF THE NEW VARIETY

The variety was discovered as a seedling by the inventor in September, 1986 near Sanger in the San Joaquin Valley of central California. The new variety was asexually reproduced by grafting wood of the new variety on Nemaguard peach rootstock. The new variety was asexually reproduced in February, 1987 under the direction of the inventor near Kerman in the San Joaquin Valley of central California. The inventor has continued to observe the asexually reproduced peach trees of the new variety and has confirmed that they are identical in all respects to the parent.

SUMMARY OF THE NEW VARIETY

The "Prima Gattie" peach tree is characterized by producing a large, high quality, semi-clingstone fruit which have superior external coloration and are ripe for commercial harvesting and shipment approximately September 2 to September 19 in the San Joaquin Valley of central California. The new variety is most closely similar to the "Carnival" peach tree, which produces fruit ripening at a similar time in the growing season. However, the fruit of the instant variety is distinguishable from the fruit of the "Carnival" peach tree in that the new variety are semi-clingstone fruit, while that of the "Carnival" peach tree is freestone. The flavor of the new variety is substantially improved over that of the "Carnival" peach tree, remaining sweet and pleasant even in heavy crop production. In addition, the coloration of the fruit of the new variety is greatly improved over that of the "Carnival" peach tree, developing from thirty percent (30%) to eighty percent (80%) red blush in both a washed and striped to dappled pattern, while in the case of the fruit of the "Carnival" peach tree, the red blush coloration extends only over from ten percent (10%) to forty percent (40%) of the fruit surface under normal growing conditions.

BRIEF DESCRIPTION OF THE DRAWING

The accompanying drawing is a color photograph showing mature fruit of the new variety including a first in top plan view showing the base thereof; a second in side elevation showing the suture thereof; a third in bottom plan view showing the apex thereof; a fourth sectioned and laid open to show the flesh and the stone cavity thereof; a fifth in side elevation; and a stone and foliage typical of the new variety of peach tree.

DETAILED DESCRIPTION

Referring more specifically to the pomological details of this new and distinct variety of peach tree, the following has been observed under the ecological conditions prevailing at the orchard of origin which is located in Western Fresno, County near the town of Rolinda. All major color code designations are by reference to the *Dictionary of Color*, by Maerz and Paul, First Edition, 1930. Common color names are also occasionally employed.

TREE

Generally: Eventual tree form and density are determined by the training system used in the orchard. The subject orchard has been trained using the standard "open vase"

system. The test orchard was propagated in 1989 on peach rootstock, and is in fifth leaf. From 90 cm (3.0 feet) to 135 cm (4.5 feet) of new growth is now occurring in the tops of the trees each year.

*Size.*—Variable. Ranges from 330 cm (11 feet) to 390 cm (13 feet) in height and from 360 cm (12 feet) to 420 cm (14 feet) in width.

*Vigor.*—Vigorous and hardy.

*Figure.*—Upright to upright-spreading in form.

*Productivity.*—Productive.

*Regularity of bearing.*—Regular under typical central San Joaquin Valley climatic conditions.

Trunk:

*Size.*—Average in thickness from 12.1 cm (4.764 inches) to 17.4 cm (6.850 inches) in diameter.

*Surface texture.*—Rough in bark texture. The bark surface is moderately scaly with a moderate amount of scarfskin present.

*Color.*—Grey-brown (7-A-9).

*Lenticels.*—Numerous bark lenticels are present, medium in size and oval in form. Length — 3.5 mm (0.138 inches) to 10.0 mm (0.398 inches). Height — 1.5 mm (0.059 inches) to 2.0 mm (0.079 inches).

Branches:

*Size.*—Average in thickness.

*Surface texture.*—Moderately rough.

*Color—Two year or older wood.*—Medium brown (7-A-11 Van Dyke Brown). Slightly striated.

*Color—immature branches.*—Pale green (19-K-6 Sea Green). Many shoots exposed to direct sunlight have a red-rose pigmentation present on the exposed side (7-J-8 Domingo Red). Color of the new shoot tip is a bright green-yellow (19-L-6 Calliste Green).

*Internode.*—Length — On bearing hanger shoots is normal, ranging from 22 mm (0.866 inches) to 30 mm (1.181 inches) between nodes as measured at mid-stem on current season's growth.

LEAVES

Size:

*Generally.*—Medium to large. Leaf measurements are from large leaves growing near midpoint of actively growing upright current season's shoots.

Average length.—19.8 cm (7.795 inches) to 22.1 cm (8.701 inches) including the leaf petiole.

Average width.—4.7 cm (1.850 inches) to (2.165 inches).

Leaf thickness: Normal.

Form: Lanceolate with acuminate tip. Leaf apices often are slightly twisted sideways and reflexed downwards.

Color:

*Upwardly disposed surface.*—Dark green (24-L-4).

*Downwardly disposed surface.*—Lighter grey-green (22-J-5 Leek Green).

Marginal form:

*Generally.*—Crenate, with broad, low, regular crenations.

Leaf margin — Moderately undulate.

Glandular characteristics: Glands are medium to large in size. Gland form is generally reniform. On the leaf blade gland number is variable, from 1 to 4 present on the base of the leaf blade. Glands present on the blade are always reniform. From 2 to 4 additional reniform glands are present on the petiole or right at the petiolar junction with the basal leaf margin. The glands are alternate in position.

Leaf gland color: Bright shiny green-yellow when young (19-L-2 Javel Green), becoming dark and deteriorating with age.

Petiole:

*Size.*—Relatively large.

*Length.*—13 mm (0.512 inches) to 16 mm (0.630 inches).

Thickness.—2.0 mm (0.079 inches).

*Color.*—Pale green (20-J-2) with a darker green coloration within the petiole groove (20-K-6 Piquant Green).

Stipules: Moderately long. The stipules are present primarily on every new shoot growth and are early deciduous.

*Length.*—8 mm (0.315 inches) to 10 mm (0.394 inches).

*Form.*—Linear lanceolate with serrate margins.

*Color.*—Bright green-yellow (18-K-6) becoming darker with age and rapidly deteriorating.

FLOWERS

Flower buds: Dormant flower buds are average in size and conic in form. Bud scale coloration is grey (55-A-2 Lead Grey). The buds are slightly appressed to the bearing stem. The bud scale surfaces are very pubescent with a dense grey colored pubescence. The buds are hardy under typical central San Joaquin Valley climatic conditions.

Date of bloom: The bloom of the new variety is slightly late in relation other commercial peach cultivars commonly grown in the central San Joaquin Valley region. Date of first bloom was February 27 in 1992, and date of full bloom was March 4 in 1992.

Bloom Quantity: Abundant. Flower number per node varies from 1 to 2 on fruitful hanger shoots.

Size:

*Generally.*—Medium to slightly below average in the middle range of this type of non-showy flower. Flower diameter fully expanded ranges from 20 mm (0.787 inches) to 24 mm (0.945 inches). The flower remains slightly cupped inward even when fully mature.

Petals:

*Size.*—Medium to small.

*Length.*—12 mm (0.472 inches) to 13 mm (0.519 inches).

*Width.*—8 mm (0.315 inches) to 10 mm (0.394 inches).

*Form.*—Variable but most frequently oval with petal margins usually rolled upwards.

*Number.*—Five.

*Color.*—Young petals are light pink (1-C-1) on the petal interior, a darker pink (1G-1) along the petal margins, and nearly white (1-A-1) on the petal claw. As the petal matures, the margins become a darker dull pink-rose (1-F-2) and the claw becomes a deep rose (1-F-5). The interior area of the petal also darkens to a medium pink (1-D-2).

*Claw form.*—Narrow and truncate in form, averaging 1 mm (0.039 inches) in length.

*Margins.*—Very undulate.

*Apex.*—The petal apices are variable in form, but are generally rounded and usually substantially undulate.

Flower pedicel:

*Size.*—Medium, ranging from 2 mm (0.079 inches) to 3 mm (0.118 inches) in length.

*Thickness.*—1.0 mm (0.039 inches).

*Color.*—Bright shiny green (17-K-6).

*Surface.*—Glabrous.

Nectaries:

*Color.*—Young nectaries are bright orange (11-I-12), darkening and becoming somewhat dull with age.

Anthers:

*Size.*—Medium to large.

*Color.*—Light yellow (10J-4 Primrose Yellow) both ventrally and dorsally.

*Pollen.*—Abundant.

Polllen:

*Color.*—Yellow (10-L-4 Light Chrome Yellow).

Stamens:

*Length.*—Moderately long ranging from 12 mm (0.472 inches) to 15 mm (0.590 inches). Stamen length is variable in relation to the pistil, at times shorter, at other times about equal.

Filament:

*Color.*—White (1-A-1) when young, turning to a deep rose (1-I-4 Casino Pink) with maturity.

Pistil:

*Length.*—Variable, ranging from 15 mm (0.590 inches) to 18 mm (0.709 inches), including the ovary.

Color.—Light yellow (11-K-1 Acacia Yellow).

Surface.—Highly pubescent.

FRUIT

Maturity when described: Firm ripe condition typical of full commercial maturity. In 1992, the first pick was on September 2 and the last pick on September 19 near Rolinda of the San Joaquin Valley of central California.

Size:

*Generally.*—Large and uniform.

*Average diameter in the check plane.*—73 mm (2.984 inches) to 80 mm (3.150 inches).

*Average diameter transverse in the suture plane.*—71 mm (2.795 inches) to 78 mm (3.071 inches).

*Average diameter in the axial plane.*—72 mm (2.835 inches) to 78 mm (3.071 inches).

Form:

*Symmetry.*—Usually asymmetrical with one fruit half larger than the other.

*Lateral.*—Variable, from ovate to nearly oval.

*Apical.*—Somewhat variable, usually globose, but at times with an elongated ventral suture area.

Suture:

*Generally.*—Relatively shallow, inconspicuous line extending from base to apex, somewhat deeper within the stem cavity basin. The suture has no distinctive coloration of its own, but takes on the coloration of the underlying blush or ground color.

Ventral surface:

*Generally.*—Slightly irregular, often with a slightly raised ventral surface, lipped on one side.

Stem cavity:

*Generally.*—Small to medium in size. The shoulders of the cavity are often creased with a groove where the fruit was attached to the bearing branch.

*Width.*—26 mm (1.024 inches) to 31 mm (1.220 inches).

*Depth.*—14 mm (0.551 inches) to 18 mm (0.709 inches).

*Length.*—29 mm (1.142 inches) to 35 mm (1.378 inches).

*Shape.*—Oval.

Stem:

*Length.*—Varies from 11 mm (0.433 inches) to 13 mm (0.512 inches).

*Thickness.*—3.0 mm (0.118 inches) to 3.5 mm (0.138 inches).

*Color.*—Light olive green (13-L-2).

Base:

*Form.*—Moderately truncate.

*Angle.*—Moderately to strongly oblique to the fruit axis.

Apex:

*Shape.*—Generally rounded with a slightly raised tip. A marked depression is present on both the ventral and dorsal side of the apex.

Pistil point:

*Position.*—Most frequently apical.

Skin:

*Thickness.*—Average. Skin is tenacious to the flesh at commercial maturity.

*Texture.*—Surface is pubescent with a medium textured, short pubescence.

*Skin flavor.*—Relatively neutral.

*Tendency to crack.*—No tendency to crack or split has been observed.

*Color.*—Generally — Skin color is a somewhat uneven, but attractive, combination of red blush color and yellow ground color. Blush color covers from thirty percent (30%) to as much as eighty percent (80%) of the fruit surface, with exterior and exposed fruit in the highest color ranges. Blush form varies from a washed pattern to light striping and dappled areas. Ground color covers from twenty percent (20%) to seventy percent (70%) of the fruit surface with the most interior fruit on the tree in the highest ground color ranges.

*Blush color.*—Intensity varies from a dark red (6-L-11 Egyptian Red) to a lighter orange-red (4-I-12 Nasturtium Red).

*Ground color.*—Light gold-yellow (10-K-5).

Flesh:

*Flesh color.*—Somewhat variable. Generally, light yellow (10-K-2) from under the skin inward for 10 mm (0.394 inches) to 14 mm (0.551 inches). Numerous light colored fibers are present within the flesh.

*Color of Stone Cavity.*—Red (5-L-10 Chimney Red) with red streaks and flecking extending outward from the cavity 10 mm (0.394 inches) to 16 mm (0.630 inches) into the flesh.

*Juice production.*—Becomes juicy with afterripening.

*Flavor.*—Sweet with moderate acidity and well balanced.

*Aroma.*—Slight and pleasant.

*Flesh Texture.*—Very firm and fine textured.

*Ripening.*—Evenly throughout.

*Eating quality.*—Good.

Stone:

*Attachment.*—Clingstone to semi-clingstone. The stone is held tightly within the cavity at commercial maturity, but will break loose from the flesh as the fruit fully ripens and softens. The stone surface is generally covered over the full surface with short fibers and small pieces of adhering flesh.

*Fibers.*—Numbers — Numerous are attached over the entire stone surface. Length — Short.

*Size.*—Generally — Medium. Length — 33 mm (1.299 inches) to 36 mm (1.417 inches). Width — 24.5 mm (0.964 inches) to 25.5 mm (1.004 inches). Thickness — 17.0 mm (0.669 inches) to 18.5 mm (0.728 inches).

*Form.*—Generally — Usually oval.

*Apex.*—Shape — Relatively variable, most frequently acute.

*Color.*—Wet — Heavily stained with a dark maroon coloration (7-L-3 Anatolia Red). Dry — Light brown (14-A-10 Leather Brown) to a darker brown-maroon (7-J-8 Domingo Brown). Substantial reddish-maroon staining is present on most stones.

*Base.*—Shape — Truncate. The base angle is usually oblique to the stone axis.

*Sides.*—Generally — Usually unequal.

*Surface.*—Moderately roughened laterally, substantially grooved over the apical shoulder area. Shallow grooves are present basally, converging basally.

*Ventral edge*—Width — Medium. 3.5 mm (0.138 inches) to 4.5 mm (0.177 inches) at mid-suture.

*Wings.*—Several low coalesced wings are present, at times slightly more prominent basally.

*Dorsal edge.*—A shallow, often discontinuous groove is present basally, less distinct over the apical shoulder. The dorsal groove is bordered by two low ridges which are at times cross cut by several grooves. The apical shoulder is slightly eroded near the stone apex.

*Hilum.*—Medium to large in size, with a thick, substantially toughened and grooved collar. Collar — The collar ranges from 2 mm (0.079 inches) to 4 mm (0.157 inches). Form — Oval.

*Tendency to split.*—No tendency to split has been observed.

Use: Fresh market.

Keeping quality: Excellent.

Shipping and handling qualities: Excellent.

Although the new variety of peach tree possesses the described characteristics noted above as a result of the growing conditions prevailing near Rolinda in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by Plant Letters Patent is:

1. A new and distinct variety of peach tree substantially as illustrated and described which produces fruit which are mature for commercial harvesting and shipment approximately September 2 to September 19 in the San Joaquin Valley of central California and which are somewhat remotely similar to the fruit of the "Carnival" peach tree, but distinguished therefrom in several respects including that they are a semi-clingstone fruit with an improved blush coloration and a sweeter, more pleasant flavor when compared with the fruit of the "Carnival" peach tree.

* * * * *

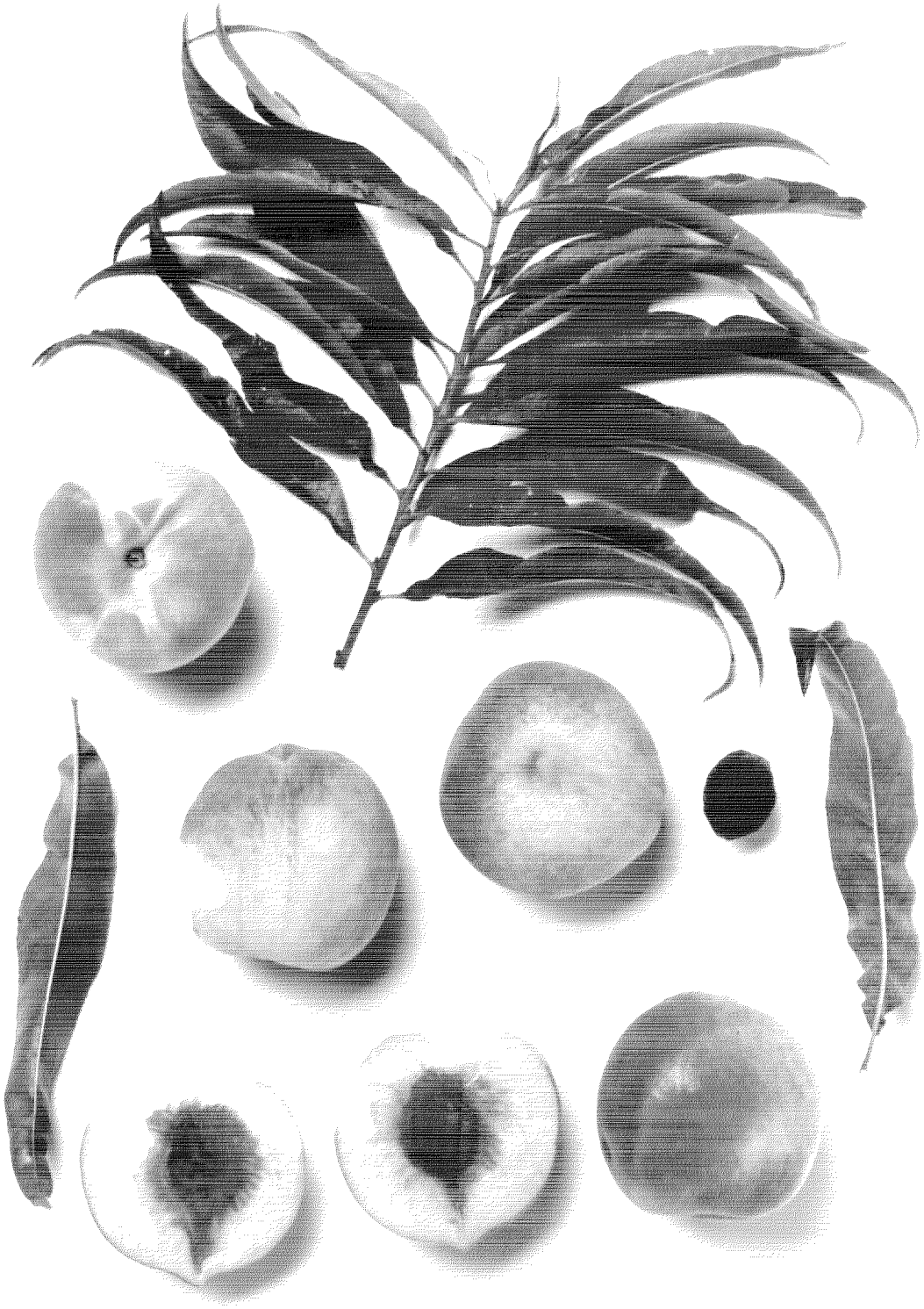

UNITED STATES PATENT AND TRADEMARK OFFICE

CERTIFICATE OF CORRECTION

PATENT NO. : Plant 10,085

DATED : October 28, 1997

INVENTOR(S) : Michael R. Gerawan

It is certified that error appears in the above-identified patent and that said Letters Patent is hereby corrected as shown below:

Column 4, Line 51, delete "(1G-1)" and substitute ---(1-G-1)---.

Column 5, Line 7, delete "(10J-4 " and substitute ---(10-J-4 ---.

Column 7, Line 29, delete "toughened" and substitute ---roughened---.

Signed and Sealed this

Third Day of February, 1998

*Attest:*

Bruce Lehman

BRUCE LEHMAN

*Attesting Officer*

*Commissioner of Patents and Trademarks*